United States Patent [19]

Schulz, Jr. et al.

[11] Patent Number: 5,811,487

[45] Date of Patent: Sep. 22, 1998

[54] THICKENING SILICONES WITH ELASTOMERIC SILICONE POLYETHERS

[75] Inventors: William James Schulz, Jr.; Shizhong Zhang, both of Midland, Mich.

[73] Assignee: Dow Corning Corporation, Midland, Mich.

[21] Appl. No.: 768,064

[22] Filed: Dec. 16, 1996

[51] Int. Cl.$^6$ .......................... C08J 83/02; C08F 283/00; C08G 77/06
[52] U.S. Cl. .......................... 524/862; 524/261; 524/588; 524/730; 524/806; 524/837; 525/479; 528/15
[58] Field of Search .................................... 524/588, 862, 524/261, 730, 806, 837; 525/479; 528/15

[56] References Cited

U.S. PATENT DOCUMENTS

| | | | |
|---|---|---|---|
| 4,056,546 | 11/1977 | Brown, Jr. | 260/448.8 |
| 4,248,751 | 2/1981 | Willing | 260/29.02 |
| 4,600,436 | 7/1986 | Traver et al. | 106/3 |
| 5,227,200 | 7/1993 | LeGrow | 427/387 |
| 5,236,986 | 8/1993 | Sakuta | 524/267 |
| 5,302,382 | 4/1994 | Kasprzak | 424/78.03 |
| 5,302,658 | 4/1994 | Gee et al. | 524/732 |
| 5,412,004 | 5/1995 | Tachibana | 524/27 |
| 5,521,245 | 5/1996 | Hirabayashi et al. | 524/493 |
| 5,539,136 | 7/1996 | Raleigh et al. | 556/420 |
| 5,654,362 | 8/1997 | Schulz, Jr. et al. | 524/862 |
| 5,665,804 | 9/1997 | Hill et al. | 524/268 |

*Primary Examiner*—James C. Housel
*Assistant Examiner*—Rodney P. Swartz
*Attorney, Agent, or Firm*—James L. DeCesare

[57] ABSTRACT

Low molecular weight siloxane fluids are thickened by silicone elastomers. The silicone elastomers are made by crosslinking reactions of ≡Si—H containing siloxanes and an unsaturated hydrocarbon such as an alpha, omega-diene, in the presence of a low molecular weight siloxane fluid. The ≡SiH siloxane is first partially reacted with a mono-alkenyl functionalized polyether. It is then crosslinked by the alpha, omega-diene, in the presence of the low molecular weight siloxane fluid. An elastomer, i.e. gel, with polyether groups is produced. The elastomer can be swollen with the low molecular weight siloxane fluid under shear force, to provide a uniform silicone paste. The silicone paste has excellent spreadability upon rubbing, and possesses unique rheological properties in being thixotropic and shear thinning. The silicone paste can be easily emulsified with water to form a stable uniform emulsion, without using a surfactant to allow normally immiscible materials to become intimately mixed.

18 Claims, No Drawings

THICKENING SILICONES WITH ELASTOMERIC SILICONE POLYETHERS

BACKGROUND OF THE INVENTION

This invention is directed to thickened low molecular weight siloxane fluids or solvents, in the form of silicone elastomers swollen into silicone gels and silicone pastes, which can be formed into silicone emulsions.

Cross-links are junctions of polymer strands in a three-dimensional network. They may be viewed as long-chain branches which are so numerous that a continuous insoluble network or gel is formed.

Increasingly, platinum catalyzed hydrosilylation reactions are being used to form networks. They typically involve reactions between a low molecular weight siloxane containing several ≡Si—H groups, and a high molecular weight siloxane containing several ≡Si-vinyl groups, or vice versa.

Attractive features of this mechanism are that (i) no by-products are formed, (ii) cross-linking sites and hence network architecture can be narrowly defined, and (iii) hydrosilylation will proceed even at room temperature to form the networks. In the mechanism, crosslinking involves addition of ≡SiH across double bonds, i.e., ≡SiH+CH$_2$=CH—R→≡SiCH$_2$CH$_2$—R; or crosslinking involves addition of ≡SiH across triple bonds, i.e., ≡SiH+HC≡C—R→≡SiCH=CH—R.

We have utilized this mechanism, but by employing some unobvious and unique modifications of the mechanism, we have been able to formulate a new range of product forms having new and unique properties and ranges of application. In particular, one unique aspect is that our silicone paste can be used to form an emulsion without the need of a surfactant. This can be of considerable value in the personal care arena where skin sensitivity due to the presence of certain surfactants can be an issue.

BRIEF SUMMARY OF THE INVENTION

Our invention relates to a method of making a silicone elastomer by a first step of reacting (A) an ≡Si—H containing polysiloxane; and (B) a mono-alkenyl polyether; in the presence of a platinum catalyst, until an ≡Si—H containing siloxane with polyether groups is formed. In a second step according to our method, we react (C) the ≡Si—H containing siloxane with polyether groups; and (D) an unsaturated hydrocarbon such as an alpha, omega-diene; in the presence of (E) a solvent and a platinum catalyst, until a silicone elastomer is formed by crosslinking and addition of ≡SiH across double bonds in the alpha, omega-diene.

As another feature of our invention, additional solvent is added to the silicone elastomer, and the solvent and silicone elastomer are sheared until a silicone paste is formed.

As a further feature of our invention, water is added to the silicone paste, and the water and silicone paste are sheared until a silicone emulsion is formed. The silicone emulsion is formed free of the presence of a surfactant.

Silicone elastomers, silicone pastes, and silicone emulsions, prepared according to these methods, have particular value and utility in treating hair, skin, or underarm areas of the human body. In addition, the silicone elastomers, silicone pastes, and silicone emulsions, are capable of forming barrier films after evaporation of any solvent or volatile component.

These and other objects and features of our invention will become apparent from a consideration of the detailed description.

DETAILED DESCRIPTION OF THE INVENTION

Our invention, and the various steps carried out according to our process, can be illustrated with reference to the procedure as shown below.

Step 1: Incorporation of the Polyether
≡SiH siloxane+mono-alkenyl polyether+platinum catalyst→≡SiH siloxane with polyether groups Step 2: Gelation
≡SiH siloxane with polyether group+≡SiH siloxane (optional)+alpha, omega-diene+low molecular weight siloxane fluid+platinum catalyst→gel (elastomer)

Step 3: Shearing and Swelling
gel/elastomer+low molecular weight siloxane fluid→paste Step 4: Emulsification
silicone paste+water+shear→silicone emulsion In Step 1, the molar ratio of the polyether to the ≡SiH in the ≡SiH siloxane should be between zero and one.

In Step 2, the weight ratio of the low molecular weight siloxane fluid to the weight of the ≡SiH siloxane with polyether groups and the alpha, omega-diene can be from 1–98, but preferably is between 3–10. The molar ratio of the ≡SiH siloxane with polyether groups and the alpha, omega-diene can be from 20:1 to 1:20, but preferably is 1:1. While Step 2 can include a mixture of various types of compounds, at least one ≡SiH containing siloxane must include a polyether group.

For example, one formulation found especially suitable for Step 2 is a mixture containing the following compounds:
Me$_3$SiO(Me$_2$SiO)$_{50}$[MeQSiO]$_4$(MeHSiO)$_5$SiMe$_3$
HSiMe$_2$O(Me$_2$SiO)$_{10}$SiHMe$_2$
Me$_3$SiO(Me$_2$SiO)$_8$(MeHSiO)$_4$SiMe$_3$
1,5-hexadiene, and decamethylcyclopentasiloxane. In these formulas, Me is methyl and Q is —CH$_2$CH$_2$CH$_2$(CH$_2$CH$_2$O)$_{10}$H.

In Step 3, the silicone paste should contain 80–98 percent by weight of the low molecular weight siloxane fluid or other fluid or solvent to be thickened.

In Step 4, the weight ratio of water to the silicone paste can be 95:5 to 5:95.

The ≡Si—H containing polysiloxane is represented by compounds of the formula R$_3$SiO(R'$_2$SiO)$_a$(R"HSiO)$_b$SiR$_3$ referred to as type A$^1$, and compounds of the formula HR$_2$SiO(R'$_2$SiO)$_c$SiR$_2$H or compounds of the formula HR$_2$SiO(R'$_2$SiO)$_a$(R"HSiO)$_b$SiR$_2$H referred to as type A$^2$. In the three formulas, R, R', and R", are alkyl groups with 1–6 carbon atoms; a is 0–250; b is 1–250; and c is 0–250. The molar ratio of compounds A$^2$:A$^1$ is 0–20, preferably 0–5. In preferred embodiments, compounds of types A$^1$ and A$^2$ are used in the reaction, however, it is possible to successfully conduct the reaction using only compounds of type A$^1$. The ≡Si—H containing polysiloxane A$^1$ can also comprise an alkylhydrogen cyclosiloxane or an alkylhydrogen-dialkyl cyclosiloxane copolymer, represented in general by the formula (R'$_2$SiO)$_a$(R"HSiO)$_b$ where R', R", a, and b, are as defined above. Preferably, a is 0–7; and b is 3–10. Some representative compounds are (OSiMeH)$_4$, (OSiMeH)$_3$(OSiMeC$_6$H$_{13}$), (OSiMeH)$_2$(OSiMeC$_6$H$_{13}$)$_2$, and (OSiMeH)(OSiMeC$_6$H$_{13}$)$_3$, where Me is —CH$_3$.

The most preferred unsaturated hydrocarbon is an alpha, omega-diene of the formula CH$_2$=CH(CH$_2$)$_x$CH=CH$_2$ where x is 1–20. Some representative examples of suitable alpha, omega-dienes for use herein are 1,4-pentadiene; 1,5-hexadiene; 1,6-heptadiene; 1,7-octadiene; 1,8-nonadiene; 1,9-decadiene; 1,11-dodecadiene; 1,13-tetradecadiene; and 1,19-eicosadiene.

However, other unsaturated hydrocarbons can be used such as alpha, omega-diynes of the formula CH≡C(CH$_2$)$_x$C≡CH; or alpha, omega-ene-ynes of the formula CH$_2$=CH(CH$_2$)$_x$C≡CH where x is 1–20. Some representative examples of suitable alpha, omega-diynes for use herein are 1,3-butadiyne HC≡C—C≡CH and 1,5-hexadiyne (dipropargyl) HC≡C—CH$_2$CH$_2$—C≡CH. One representative example of a suitable alpha, omega-ene-yne for use herein is hexene-5-yne-1 CH$_2$=CHCH$_2$CH$_2$C≡CH.

The reactions in Steps 1 and 2 requires a catalyst to effect the reaction between the ≡SiH containing siloxanes, the mono-alkenyl polyether, and the alpha, omega-diene. Suitable catalysts are Group VIII transition metals, i.e., the noble metals. Such noble metal catalysts are described in U.S. Pat. No. 3,923,705, incorporated herein by reference, to show platinum catalysts. One preferred platinum catalyst is Karstedt's catalyst, which is described in Karstedt's U.S. Pat. Nos. 3,715,334 and 3,814,730, incorporated herein by reference. Karstedt's catalyst is a platinum divinyl tetramethyl disiloxane complex, typically containing about one weight percent of platinum, carried in a polydimethylsiloxane fluid or in a solvent such as toluene. The particular catalyst used in our examples was 20 μl and 200 μl portions of Karstedt catalyst as one weight percent of platinum carried in a two centistoke (mm$^2$/s) polydimethylsiloxane fluid. Another preferred platinum catalyst is a reaction product of chloroplatinic acid and an organosilicon compound containing terminal aliphatic unsaturation. It is described in U.S. Pat. No. 3,419,593, incorporated herein by reference. The noble metal catalysts are used in amounts from 0.00001–0.5 parts per 100 weight parts of ≡SiH containing polysiloxane, preferably 0.00001–0.02 parts, most preferably 0.00001–0.002 parts.

The mono-alkenyl polyether is a compound of the formula CH$_2$=CH(CH$_2$)$_x$O(CH$_2$CH$_2$O)$_y$(CH$_2$CH$_3$CHO)$_z$T, or a compound of the formula CH$_2$=CH-Q-O(CH$_2$CH$_2$O)$_y$(CH$_2$CH$_3$CHO)$_z$T. In the formulas, T represents an end group which can be hydrogen; a C1–C10 alkyl group such as methyl, ethyl, propyl, butyl, and decyl; an aryl group such as phenyl; or a C1–C20 acyl group such as acetyl, propionyl, butyryl, lauroyl, myristoyl, and stearoyl. Q is a divalent linking group containing unsaturation such as phenylene —C$_6$H$_4$—. The value of x is 1–6; y can be zero or have a value of 1–100; z can be zero or have a value of 1–100; with the proviso that y and z cannot both be zero.

The low molecular weight siloxane fluid can be (i) a low molecular weight linear or cyclic volatile methyl siloxane; (ii) a low molecular weight linear or cyclic, volatile or non-volatile, alkyl or aryl siloxane; or (iii) a low molecular weight linear or cyclic functional siloxane. Most preferred, however, is a low molecular weight linear or cyclic volatile methyl siloxane (VMS).

VMS compounds have the average unit formula (CH$_3$)$_a$SiO$_{(4-a)/2}$ where a has an average value of two to three. The compounds contain siloxane units joined by ≡Si—O—Si≡ bonds. Representative units are monofunctional "M" units (CH$_3$)$_3$SiO$_{1/2}$ and difunctional "D" units (CH$_3$)$_2$SiO$_{2/2}$.

The presence of trifunctional "T" units CH$_3$SiO$_{3/2}$ results in the formation of branched linear or cyclic volatile methyl siloxanes. The presence of tetrafunctional "Q" units SiO$_{4/2}$ results in the formation of branched linear or cyclic volatile methyl siloxanes.

Linear VMS have the formula (CH$_3$)$_3$SiO{(CH$_3$)$_2$SiO}$_y$Si(CH$_3$)$_3$. The value of y is 0–5. Cyclic VMS have the formula {(CH$_3$)$_2$SiO}$_z$. The value of z is 3–8, preferably 3–6. These volatile methyl siloxanes generally have a boiling point less than about 250° C., and a viscosity of 0.65–5.0 centistokes (mm$^2$/s).

These volatile methyl siloxanes can be represented by:

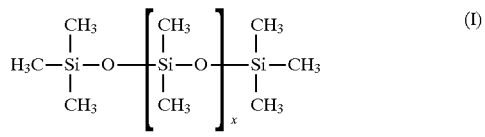

Linear

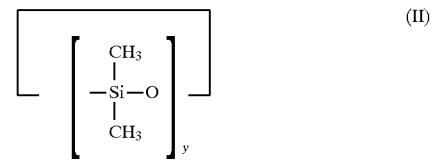

Cyclic

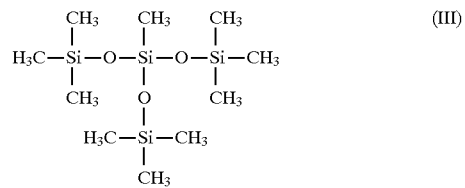

Branched Linear

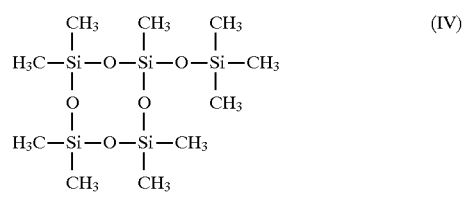

Branched Cyclic

Some representative linear volatile methyl siloxanes (I) are hexamethyldisiloxane (MM) with a boiling point of 100° C., viscosity of 0.65 mm$^2$/s, and formula Me$_3$SiOSiMe$_3$; octamethyltrisiloxane (MDM) with a boiling point of 152° C., viscosity of 1.04 mm$^2$/s, and formula Me$_3$SiOMe$_2$SiOSiMe$_3$; decamethyltetrasiloxane (MD$_2$M) with a boiling point of 194° C., viscosity of 1.53 mm$^2$/s, and formula Me$_3$SiO(Me$_2$SiO)$_2$SiMe$_3$; dodecamethylpentasiloxane (MD$_3$M) with a boiling point of 229° C., viscosity of 2.06 mm$^2$/s, and formula Me$_3$SiO(Me$_2$SiO)$_3$SiMe$_3$; tetradecamethylhexasiloxane (MD$_4$M) with a boiling point of 245° C., viscosity of 2.63 mm2/s, and formula Me$_3$SiO(Me$_2$SiO)$_4$SiMe$_3$; and hexadecamethylheptasiloxane (MD$_5$M) with a boiling point of 270° C., viscosity of 3.24 mm$^2$/s, and formula Me$_3$SiO(Me$_2$SiO)$_5$SiMe$_3$.

Some representative cyclic volatile methyl siloxanes (II) are hexamethylcyclotrisiloxane (D$_3$) a solid with a boiling point of 134° C. and formula {(Me$_2$)SiO}$_3$; octamethylcyclotetrasiloxane (D$_4$) with a boiling point of 176° C., viscosity of 2.3 mm$^2$/s, and formula {(Me$_2$)SiO}$_4$; decamethylcyclopentasiloxane (D$_5$) with a boiling point of 210° C., viscosity of 3.87 mm$^2$/s, and formula {(Me$_2$)SiO}$_5$; and dodecamethylcyclohexasiloxane (D$_6$) with a boiling point of 245° C., viscosity of 6.62 mm$^2$/s, and formula {(Me$_2$)SiO}$_6$.

Some representative branched volatile methyl siloxanes (III) and (IV) are heptamethyl-3-{(trimethylsilyl)oxy}trisiloxane (M$_3$T) with a boiling point of 192° C., viscosity of 1.57 mm$^2$/s, and formula C$_{10}$H$_{30}$O$_3$Si$_4$; hexamethyl-3,3,bis {(trimethylsilyl)oxy}trisiloxane (M$_4$Q) with a boiling point of 222° C., viscosity of 2.86 mm$^2$/s, and formula C$_{12}$H$_{36}$O$_4$Si$_5$; and pentamethyl {(trimethylsilyl)oxy} cyclotrisiloxane (MD$_3$) with the formula C$_8$H$_{24}$O$_4$Si$_4$.

Our process can also include the use of low molecular weight linear or cyclic, volatile or non-volatile, alkyl and aryl siloxanes. Representative linear siloxanes are compounds of the formula $R_3SiO(R_2SiO)_ySiR_3$, and representative cyclic siloxanes are compounds of the formula $(R_2SiO)_z$. R is an alkyl group of 2–6 carbon atoms, or an aryl group such as phenyl. The value of y is 0–80, preferably 0–20. The value of z is 0–9, preferably 4–6. These siloxanes have a viscosity generally in the range of about 1–100 centistokes (mm$^2$/s).

Other representative low molecular weight non-volatile siloxanes have the general structure:

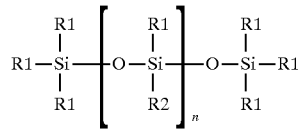

where n has a value to provide the polymer with a viscosity in the range of about 100–1,000 centistokes (mm$^2$/sec).

R1 and R2 are alkyl radicals of 2–20 carbon atoms, an aryl group such as phenyl, or a functional group. Typically, the value of n is about 80–375. Illustrative siloxanes are polydiethylsiloxane, polymethylethylsiloxane, polymethylphenylsiloxane, and polydiphenylsiloxane.

Low molecular weight functional siloxanes can be represented by acrylamide functional siloxane fluids, acrylate functional siloxane fluids, amide functional siloxane fluids, amino functional siloxane fluids, carbinol functional siloxane fluids, carboxy functional siloxane fluids, chloroalkyl functional siloxane fluids, epoxy functional siloxane fluids, glycol functional siloxane fluids, ketal functional siloxane fluids, mercapto functional siloxane fluids, methyl ester functional siloxane fluids, perfluoro functional siloxane fluids, and silanol functional siloxanes.

Our invention is not limited to swelling silicone elastomers with only low molecular weight siloxane fluids. Other types of solvents can be used to swell the silicone elastomer, and a single solvent or a mixture of solvents may be used.

Therefore, by solvent we mean (i) organic compounds, (ii) compounds containing a silicon atom, (iii) mixtures of organic compounds, (iv) mixtures of compounds containing a silicon atom, or (v) mixtures of organic compounds and compounds containing a silicon atom. This definition contemplates that the compound(s) are used on an industrial scale to dissolve, suspend, or change the physical properties, of other materials.

In general, the organic compounds can be aromatic hydrocarbons, aliphatic hydrocarbons, alcohols, aldehydes, ketones, amines, esters, ethers, glycols, glycol ethers, alkyl halides, or aromatic halides. Representative of some of the more common organic solvents are alcohols such as methanol, ethanol, 1-propanol, cyclohexanol, benzyl alcohol, 2-octanol, ethylene glycol, propylene glycol, and glycerol; aliphatic hydrocarbons such as pentane, hexane, cyclohexane, heptane, VM&P solvent, and mineral spirits; alkyl halides such as chloroform, carbon tetrachloride, perchloroethylene, ethyl chloride, and chlorobenzene; amines such as isopropylamine, cyclohexylamine, ethanolamine, and diethanolamine; aromatic hydrocarbons such as benzene, toluene, ethylbenzene, and xylene; esters such as ethyl acetate, isopropyl acetate, ethyl acetoacetate, amyl acetate, isobutyl isobutyrate, and benzyl acetate; ethers such as ethyl ether, n-butyl ether, tetrahydrofuran, and 1,4-dioxane; glycol ethers such as ethylene glycol monomethyl ether, ethylene glycol monomethyl ether acetate, diethylene glycol monobutyl ether, and propylene glycol monophenyl ether; ketones such as acetone, methyl ethyl ketone, cyclohexanone, diacetone alcohol, methyl amyl ketone, and diisobutyl ketone; petroleum hydrocarbons such as mineral oil, gasoline, naphtha, kerosene, gas oil, heavy oil, and crude oil; lubricating oils such as spindle oil and turbine oil; and fatty oils such as corn oil, soybean oil, olive oil, rape seed oil, cotton seed oil, sardine oil, herring oil, and whale oil.

Other miscellaneous organic solvents can also be used, such as acetonitrile, nitromethane, dimethylformamide, propylene oxide, trioctyl phosphate, butyrolactone, furfural, pine oil, turpentine, and m-creosol.

We further intend to encompass by the term solvent, volatile flavoring agents such as oil of wintergreen; peppermint oil; spearmint oil; menthol; vanilla; cinnamon oil; clove oil; bay oil; anise oil; eucalyptus oil; thyme oil; cedar leaf oil; oil of nutmeg; oil of sage; cassia oil; cocoa; licorice; high fructose corn syrup; citrus oils such as lemon, orange, lime, and grapefruit; fruit essences such as apple, pear, peach, grape, strawberry, raspberry, cherry, plum, pineapple, and apricot; and other useful flavoring agents including aldehydes and esters such as cinnamyl acetate, cinnamaldehyde, eugenyl formate, p-methylanisole, acetaldehyde, benzaldehyde, anisic aldehyde, citral, nerol, decanal, vanillin, tolyl aldehyde, 2,6-dimethyloctanal, and 2-ethyl butyraldehyde.

In addition, we intend the term solvent to include volatile fragrances such as natural products and perfume oils. Some representative natural products and perfume oils are ambergris, benzoin, civet, clove, leaf oil, jasmine, mate', mimosa, musk, myrrh, orris, sandalwood oil, and vetivert oil; aroma chemicals such as amyl salicylate, amyl cinnamic aldehyde, benzyl acetate, citronellol, coumarin, geraniol, isobornyl acetate, ambrette, and terpinyl acetate; and the various classic family perfume oils such as the floral bouquet family, the oriental family, the chypre family, the woody family, the citrus family, the canoe family, the leather family, the spice family, and the herbal family.

The process is carried out stepwise by combining the ≡SiH containing siloxane(s), the mono-alkenyl polyether, the alpha, omega-diene, the low molecular weight siloxane or solvent, and the platinum catalyst; and mixing these ingredients at room temperature until a gel, elastomer, paste, or emulsion, is formed. If desired, the gel, elastomer, paste, or emulsion, can be further diluted with an additional similar or dissimilar solvent(s), to form the final composition. A blend of hexane and tetrahydrofuran, a fragrance, an oil, or another low molecular weight siloxane, are examples of diluents that could be so employed. Higher temperatures to speed up the process can be used.

Additional amounts of low molecular weight siloxane or solvent are added to the gel, i.e., Step 3, and the resulting mixture is subjected to shear force to form the paste. In Step 4, shear force is again used, during or after water is added to the paste to form the emulsion. Any type of mixing and shearing equipment may be used to perform these steps such as a batch mixer, planetary mixer, single or multiple screw extruder, dynamic or static mixer, colloid mill, homogenizer, sonolator, or a combination thereof.

Typically, we carry out the process using approximately a 1:1 molar ratio of the ≡Si—H containing siloxane with polyether groups and the alpha, omega-diene. It is expected that useful materials may also be prepared by carrying out the process with an excess of either the ≡Si—H containing siloxane or the alpha, omega-diene, but this would be considered a less efficient use of the materials. The remainder of the composition comprises the low molecular weight siloxane or solvent, in amounts generally within the range of about 65–98 percent by weight of the composition, but preferably about 80–98 percent by weight.

The following examples are set forth for the purpose of illustrating our invention in more detail.

EXAMPLE 1

100 g of an organopolysiloxane with the average structure $Me_3SiO(Me_2SiO)_{93}(MeHSiO)_6SiMe_3$ and 6.07 g $CH_2$=$CHCH_2O(CH_2CH_2O)_7H$ were mixed with 100 g 2-propanol in a three-neck round bottom flask. To this solution, 200 $\mu l$ Karstedt catalyst (i.e., one weight percent platinum in two centistoke ($mm^2$/s) polydimethylsiloxane fluid) was added. The solution was stirred and heated to maintain it at approximately 70° C. After 1 hour, the three-neck flask was connected to a vacuum pump, and evacuated to remove 2-propanol. A polyether branched ≡SiH siloxane polymer was obtained in almost quantitative yield.

16 grams of the polyether branched ≡SiH siloxane polymer and 0.411 g 1,5-hexadiene were mixed with 65.64 g decamethylcyclopentasiloxane in a reaction vessel. 20 $\mu l$ Karstedt catalyst was added while the solution was stirred. Gelation occurred within a few hours. The gel was left in the reactor overnight before 50 parts by weight of the gel were swollen by 50 parts by weight of decamethylcyclopentasiloxane under shear force. A uniform paste was obtained having a viscosity at a shear rate of 0.02 $s^{-1}$, of 1.82×$10^6$ cP/mPa.s.

This uniform paste and deionized water in a 1:1 weight ratio were mixed in a glass jar with a mechanical stirrer, and a white emulsion was formed with excellent aesthetics and stability. No surfactant was required to form this emulsion.

EXAMPLE 2

100 g of an organopolysiloxane with the average structure $Me_3SiO(Me_2SiO)_{108}(MeHSiO)_{10}SiMe_3$ and 12.42 g $CH_2$=$CHCH_2O(CH_2CH_2O)_{10}[CH(CH_3)\ CH_2O]_4H$ were mixed with 100 g 2-propanol in a three-neck round bottom flask. To this solution, 200 $\mu l$ Karstedt catalyst was added. The solution was stirred and heated to maintain it at approximately 70° C. After 1 hour, the three-neck flask was connected to a vacuum pump, and evacuated to remove 2-propanol. A polyether branched ≡SiH siloxane polymer was obtained in almost quantitative yield.

12 grams of the polyether branched ≡SiH siloxane polymer and 0.72 g 1,9-decadiene were mixed with 65.64 g decamethylcyclopentasiloxane in a reaction vessel. 20 $\mu l$ Karstedt catalyst was added while the solution was stirred. Gelation occurred within a few hours. The gel was left in the reactor overnight before 50 parts by weight of the gel were swollen by 26 parts by weight of decamethylcyclopentasiloxane under shear force. A uniform paste was obtained having a coefficient of viscosity at a shear rate per second of 0.02 $s^{-1}$, of 2.66×$10^6$ cP/mPa.s.

This uniform paste and deionized water in a 1:1 weight ratio were mixed in a glass jar with a mechanical stirrer, and a white emulsion was formed with excellent aesthetics and stability. The emulsion had a viscosity at a shear rate of 0.02 $s^{-1}$, 4.93×$10^6$ cP/mPa.s. Again, no surfactant was required to form this emulsion.

EXAMPLE 3

100 g of an organopolysiloxane with the average structure $Me_3SiO(Me_2SiO)_{93}(MeHSiO)_6SiMe_3$ and 7.99 g $CH_2$=$CHCH_2O(CH_2CH_2O)_7H$ were mixed with 100 g 2-propanol in a three-neck round bottom flask. To this solution, 200 $\mu l$ Karstedt catalyst was added. The solution was stirred and heated to maintain it at approximately 70° C. After 1 hour, the three-neck flask was connected to a vacuum pump, and evacuated to remove 2-propanol. A polyether branched ≡SiH siloxane polymer was obtained in almost quantitative yield.

12 grams of the above polyether branched ≡SiH siloxane polymer, 1.5 g of a siloxane with the average structure $Me_3SiO(Me_2SiO)_{16}(MeHSiO)_{39}SiMe_3$, and 0.925 g 1,5-hexadiene were mixed with 84.8 g decamethylcyclopentasiloxane in a reaction vessel. 20 $\mu l$ Karstedt catalyst was added while the solution was stirred. Gelation occurred within a few hours. The gel was left in the reactor overnight before 75 parts by weight of the gel were swollen by 50 parts by weight of decamethylcyclopentasiloxane under shear force. A uniform paste was obtained having a viscosity at a shear rate of 0.02 $s^{-1}$, of 6.6×$10^5$ cP/mPa.s.

This uniform paste and deionized water in a 1:1 weight ratio were mixed in a glass jar with a mechanical stirrer, and a white emulsion was formed with excellent aesthetics and stability. The emulsion had a viscosity at a shear rate of 0.02 $s^{-1}$, of 2.7×$10^6$ cP/mPa.s. Again, no surfactant was required to form this emulsion.

This example is illustrative of an alternate embodiment of Step 2 shown above, in which an "optional" ≡SiH siloxane is included as a component.

EXAMPLE 4

First Comparative Example

The ≡SiH containing siloxane $Me_3SiO(Me_2SiO)_{93}(MeHSiO)_6SiMe_3$ was crosslinked with 1,5-hexadiene in decamethylcyclopentasiloxane using the proportions and procedure in Example 1. A gel was formed, and the gel was then swollen with additional decamethylcyclopentasiloxane. The result was the formation of a smooth, transparent paste. However, when the paste was mixed with water, the water could not be dispersed. This example shows the effect of omitting the mono-alkenyl functionalized polyether.

EXAMPLE 5

Second Comparative Example

A polyether branched ≡SiH siloxane polymer was prepared from 100 g $Me_3SiO(Me_2SiO)_{93}(MeHSiO)_6SiMe_3$ and 6.07 g $CH_2$=$CHCH_2O(CH_2CH_2O)_7H$ using the procedure in Example 1. One gram of the above polyether branched ≡SiH siloxane polymer, 10 g of decamethylcyclopentasiloxane, and 11 g of deionized water, were then mixed. The mixture appeared to emulsify under vigorous mixing using a mechanical stirrer, and a milk-like emulsion appeared to form. However, in about two hours, the emulsion separated into two phases. This shows the effect of omitting the crosslinking reaction by an alpha, omega-diene.

The silicone elastomer, silicone gel, silicone paste, and silicone emulsion of our invention have particular value in the personal care arena. Because of the unique volatility characteristics of the VMS component of these compositions, they can be used alone, or blended with other cosmetic fluids, to form a variety of over-the-counter (OTC) personal care products.

Thus, they are useful as carriers in antiperspirants and deodorants, since they leave a dry feel, and do not cool the skin upon evaporation. They are lubricious and improve the properties of skin creams, skin care lotions, moisturizers, facial treatments such as acne or wrinkle removers, personal and facial cleansers, bath oils, perfumes, colognes, sachets, sunscreens, pre-shave and after-shave lotions, liquid soaps, shaving soaps, and shaving lathers. They can be used in hair shampoos, hair conditioners, hair sprays, mousses, permanents, depilatories, and cuticle coats, to enhance gloss and drying time, and provide conditioning benefits.

In cosmetics, they function as leveling and spreading agents for pigments in make-ups, color cosmetics, foundations, blushes, lipsticks, lip balms, eyeliners, mascaras, oil removers, color cosmetic removers, and powders. They are useful as delivery systems for oil and water soluble substances such as vitamins. When incorporated into sticks, gels, lotions, aerosols, and roll-ons, the compositions impart a dry, silky-smooth, payout.

In addition, the compositions exhibit other advantageous and beneficial properties such as clarity, shelf stability, and ease of preparation. Hence, they can have wide application, but especially in antiperspirants, deodorants, in perfumes as a carrier, and for conditioning hair.

Our silicone elastomers, gels, pastes, and emulsions, have uses beyond the personal care arena, however, including their use as a filler or insulation material for electrical cable, a soil or water barrier for in-ground stabilization, or as a replacement for epoxy materials used in coil-on-plug designs in the electronics industry.

They are also useful as carrier for crosslinked silicone rubber particles. In that application, (i) they allow ease of incorporation of the particles into such silicone or organic phases as sealants, paints, coatings, greases, adhesives, antifoams, and potting compounds; and (ii) they provide for modifying rheological, physical, or energy absorbing properties of such phases in either their neat or finished condition.

In addition, our silicone elastomers, gels, pastes, and emulsions, are capable of functioning as carriers for pharmaceuticals, biocides, herbicides, pesticides, and other biologically active substances; and they can be used to incorporate water and water-soluble substances into hydrophobic systems. Examples of some water-soluble substances are salicylic acid, glycerol, enzymes, and glycolic acid.

Where barrier films are required, the silicone elastomers, gels, pastes, and emulsions, can be applied to the surface of a substrate, such that when the solvent or low molecular weight siloxane evaporates, it leaves behind a fine powder-like particulate film on the substrate surface.

Other variations may be made in compounds, compositions, and methods described herein, without departing from the essential features of our invention. The forms of our invention are exemplary only, and not intended as limitations on its scope, as defined in the appended claims.

We claim:

1. A method of making a silicone elastomer comprising reacting:

(A) an $\equiv$Si—H containing polysiloxane of the formula $R_3SiO(R'_2SiO)_a(R"HSiO)_bSiR_3$ or the formula $(R'_2SiO)_a(R"HSiO)_b$, and optionally an $\equiv$Si—H containing polysiloxane of the formula $HR_2SiO(R'_2SiO)_cSiR_2H$ or an $\equiv$Si—H containing polysiloxane of the formula $HR_2SiO(R'_2SiO)_a(R"HSiO)_bSiR_2H$, where R, R', and R" are alkyl groups with 1–6 carbon atoms, a is 0–250, b is 1–250, and c is 0–250; and (B) a mono-alkenyl polyether of the formula $CH_2$=CH $(CH_2)_xO(CH_2CH_2O)_y(CH_2CH_3CHO)_zT$, or the formula $CH_2$=CH-Q-O$(CH_2CH_2O)_y(CH_2CH_3CHO)_zT$, where T is hydrogen, a $C_1$–$C_{10}$ alkyl group, an aryl group, or a $C_1$–$C_{20}$ acyl group; Q is a divalent linking group containing unsaturation; x is 1–6, y is zero or 1–100; and z is zero or 1–100; provided y and z are both not zero; in the presence of a platinum catalyst, until an $\equiv$Si—H containing polysiloxane with polyether groups is formed; and reacting:

(C) the $\equiv$Si—H containing polysiloxane with polyether groups;

(D) an unsaturated hydrocarbon selected from the group consisting of alpha, omega-dienes of the formula $CH_2$=CH$(CH_2)_x$CH=$CH_2$, alpha, omega-diynes of the formula CH$\equiv$C$(CH_2)_x$C$\equiv$CH, and alpha, omega-ene-ynes of the formula $CH_2$=CH$(CH_2)_x$C$\equiv$CH, where x is 1–20; in the presence of (E) a solvent selected from the group consisting of (i) organic compounds, (ii) compounds containing a silicon atom, (iii) mixtures of organic compounds, (iv) mixtures of compounds containing a silicon atom, and (v) mixtures of organic compounds and compounds containing a silicon atom; and in the presence of a platinum catalyst, until a silicone elastomer is formed by crosslinking and addition of $\equiv$SiH across double or triple bonds in the unsaturated hydrocarbon.

2. A method according to claim 1 including the further steps of adding additional amounts of the solvent to the silicone elastomer, and shearing the solvent and silicone elastomer until a silicone paste is formed.

3. A method according to claim 2 including the further steps of adding water to the silicone paste, and shearing the water and silicone paste until a silicone emulsion is formed.

4. A method according to claim 3 in which the silicone emulsion is formed free of the presence of a surfactant.

5. A method according to claim 1 in which the second step includes as an additional reactant (F) an $\equiv$Si—H containing polysiloxane of the formula $R_3SiO(R'_2SiO)_a(R'HSiO)_bSiR_3$ or the formula $(R'_2SiO)_a(R"HSiO)_b$, and optionally an $\equiv$Si—H containing polysiloxane of the formula $HR_2SiO$ $(R'_2SiO)_cSiR_2H$ or an $\equiv$Si—H containing polysiloxane of the formula $HR_2SiO(R'_2SiO)_a(R"HSiO)_bSiR_2H$, where R, R', and R" are alkyl groups with 1–6 carbon atoms, a is 0–250, b is 1–250, and c is 0–250.

6. A method according to claim 1 in which the solvent is a linear volatile methyl siloxane of the formula $(CH_3)_3SiO\{(CH_3)_2SiO\}_ySi(CH_3)_3$ where y is 0–5, or a cyclic volatile methyl siloxane of the formula $\{(CH_3)_2SiO\}_z$ where z is 3–8, the volatile methyl siloxane have a boiling point less than about 250° C. and a viscosity of 0.65–5.0 centistokes (mm$^2$/s).

7. A silicone elastomer prepared according to the method defined in claim 1.

8. A silicone paste prepared according to the method defined in claim 2.

9. A silicone emulsion prepared according to the method defined in claim 3.

10. A method of treating hair, skin, or underarm comprising applying to the hair, skin, or underarm the silicone elastomer of claim 7.

11. A method of treating hair, skin, or underarm comprising applying to the hair, skin, or underarm the silicone paste of claim 8.

12. A method of treating hair, skin, or underarm comprising applying to the hair, skin, or underarm the silicone emulsion of claim 9.

13. A method of providing a barrier film to the surface of a substrate comprising applying to the substrate the silicone elastomer of claim 7, and allowing the solvent to evaporate.

14. A method of providing a barrier film to the surface of a substrate comprising applying to the substrate the silicone paste of claim 8, and allowing the solvent to evaporate.

15. A method of providing a barrier film to the surface of a substrate comprising applying to the substrate the silicone emulsion of claim 9, and allowing the solvent to evaporate.

16. A method according to claim 1 in which the molar ratio of the mono-alkenyl polyether to the ≡SiH in the ≡SiH containing polysiloxane is between zero and one.

17. A method according to claim 16 in which the weight ratio of the solvent to the weight of the ≡SiH containing polysiloxane with polyether groups and the unsaturated hydrocarbon is 1–98.

18. A method according to claim 17 in which the molar ratio of the ≡SiH containing polysiloxane with polyether groups and the unsaturated hydrocarbon is 20:1 to 1:20.

* * * * *